US00PP17654P2

(12) United States Plant Patent
Stever

(10) Patent No.: US PP17,654 P2
(45) Date of Patent: Apr. 24, 2007

(54) ***HYDRANGEA* PLANT NAMED 'SUMMER FROST'**

(50) Latin Name: *Hydrangea macrophylla*
Varietal Denomination: Summer Frost

(75) Inventor: Karen R. Stever, Gainesville, GA (US)

(73) Assignee: Itsaul Plants, Alpharetta, GA (US)

( * ) Notice: Subject to any disclaimer, the term of this patent is extended or adjusted under 35 U.S.C. 154(b) by 0 days.

(21) Appl. No.: 11/293,736

(22) Filed: Dec. 2, 2005

(51) Int. Cl.
*A01H 5/00* (2006.01)

(52) U.S. Cl. ..... Plt./250

(58) Field of Classification Search ..... Plt./250
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Hydrangea* plant named 'Summer Frost', characterized by its Upright and somewhat outwardly spreading growth habit; green and yellow green variegated leaves; and lacecap type inflorescences with light purple-colored flowers.

1 Drawing Sheet

Botanical designation: *Hydrangea macrophylla.*
Cultivar denomination: 'Summer Frost'.

BACKGROUND OF THE INVENTION

The present Invention relates to a new and distinct cultivar of *Hydrangea* plant, botanically known as *Hydrangea macrophylla,* and hereinafter referred to by the cultivar name Summer Frost.

The new *Hydrangea* originated from an open-pollination during the summer of 1998, of an unnamed selection of *Hydrangea macrophylla,* not patented, as the female, or seed, parent with an unknown selection of *Hydrangea macrophylla.* The cultivar Summer Frost was discovered and selected by the Inventor as a single plant within the progeny of the stated open-pollination in a controlled environment in Chamblee, Ga. during the summer of 1999.

Asexual reproduction of the new cultivar by vegetative cuttings in Chamblee, Ga. since 2001, has shown that the unique features of this new *Hydrangea* are stable and reproduced true to type in successive generations.

SUMMARY OF THE INVENTION

Plants of the cultivar Summer Frost have not been observed under all possible environmental conditions. The phenotype may vary somewhat with variations in environment such as temperature and light intensity without, however, any variance in genotype.

The following traits have been repeatedly observed and are determined to be the unique characteristics of 'Summer Frost'. These characteristics in combination distinguish 'Summer Frost' as a new and distinct cultivar:

1. Upright and somewhat outwardly spreading growth habit.
2. Green and yellow green variegated leaves.
3. Lacecap type inflorescences with light purple-colored flowers.

Plants of the new *Hydrangea* can be compared to plants of the female parent selection primarily in leaf color as plants of the female parent selection have green-colored leaves.

Plants of the new *Hydrangea* can also be compared to plants of the *Hydrangea macrophylla* cultivar Blue Billow, not patented. In side-by-side comparisons conducted in Chamblee, Ga., plants of the new *Hydrangea* differed from plants of the cultivar Blue Billow in the following characteristics:

1. Plants of the new *Hydrangea* were more compact than plants of the cultivar Blue Billow.
2. Plants of the new *Hydrangea* and the cultivar Blue Billow differed in leaf coloration as plants of the cultivar Blue Billow had green-colored leaves.

BRIEF DESCRIPTION OF THE PHOTOGRAPH

The accompanying colored photograph illustrates the unique appearance of the new cultivar, showing the colors as true as it is reasonably possible to obtain in colored reproductions of this type. Colors in the photograph may differ from the color values cited in the detailed botanical description which accurately describe the colors of the new *Hydrangea.* The photograph is a top perspective view of a typical plant of 'Summer Frost'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photograph and in the following description were grown in Chamblee, Ga. in an outdoor nursery and under conditions which closely approximate commercial production conditions. Plants were about two years old when the photograph and description were taken. The photograph and description were taken during the summer.

Botanical classification: *Hydrangea macrophylla* cultivar Summer Frost.

Parentage:

*Female, or seed, parent.*—Unnamed selection of *Hydrangea macrophylla,* not patented.

*Female, or seed, parent.*—Unknown selection of *Hydrangea macrophylla,* not patented.

Propagation:

*Type cutting.*—By vegetative cuttings.

*Time to initiate roots, summer.*—About two weeks at 27° C.

*Time to initiate roots, winter.*—About three weeks at 22° C.

*Time to produce a rooted cutting or liner, summer.*—About six weeks at 27° C.

*Time to produce a rooted cutting or liner, winter.*—About eight weeks at 22° C.

*Root description.*—Fine and fibrous; white in color.

*Rooting habit.*—Freely branching.

Plant description:

*Form/growth habit.*—Upright and somewhat outwardly spreading plant habit; bushy perennial shrub.

*Plant height, soil level to top of plant plane.*—About 38 cm.

*Plane diameter or area of spread.*—About 48 cm.

*Branching habit.*—When pinched, freely branching with lateral branches potentially developing at every node.

*Lateral branches.*—Length: About 35 cm. Diameter: About 6 mm. Internode length: About 2.3 cm. Texture: New growth, smooth; mature, woody and without lenticels. Color: Developing stems: Close to 144A. Mature stems: Closest to 199D.

*Foliage description.*—Arrangement: Opposite, simple. Length: About 11 cm. Width: About 7 cm. Shape: Ovate. Apex: Acute to acuminate. Base: Obtuse. Margin: Serrate. Texture, upper and lower surfaces: Glabrous; rugose. Venation pattern: Pinnate. Color: Developing foliage, upper surface: Close to 154D. Developing foliage, lower surface: Close to 11D. Fully expanded foliage, upper surface: More green than 147A with variable and random areas of 154D. Fully expanded foliage, lower surface: Close to 147B with variable and random areas of 11D. Venation, upper surface: Close to 11D. Venation, lower surface: Close to 157D. Petiole: Length: About 1.5 cm. Diameter: About 3.5 mm. Texture, upper and lower surfaces: Smooth, glabrous. Color, upper and lower surfaces: Close to 145C.

Flower description:

*Flower type and habit.*—Single fertile and sterile flowers arranged on flattened terminal clusters in a lacecap formation. Sterile flowers with large showy sepals without petals and reproductive organs. Fertile flowers small with petals, sepals and reproductive organs. Flowers face upward and outwardly. Flowers persistent. Flowers not fragrant.

*Natural flowering season.*—Continuously flowering during the early summer in Chamblee, Ga.

*Flower longevity.*—Flowers last about two to three months on the plant.

*Quantity of flowers.*—Freely flowering; about eight sterile flowers and about 100 fertile flowers per terminal cluster.

*Inflorescence diameter.*—About 12 cm.

*Inflorescence height.*—About 6 cm.

*Flower diameter.*—Fertile flowers: About 3 mm. Sterile flowers: About 2.5 cm.

*Flower depth (height).*—Fertile flowers: About 3 mm. Sterile flowers: About 2.5 mm.

*Flower buds (fertile and sterile flowers).*—Length: About 3 mm. Diameter: About 2 mm. Shape: Obovate. Color: Close to 146C.

*Petals (petals present only on fertile flowers; sterile flowers do not have petals).*—Quantity per flower: About four. Length: About 1 mm. Width: About 1 mm. Shape: Ovate. Apex: Acute. Base: Truncate. Margin: Entire. Texture, upper and lower surfaces: Smooth, glabrous. Color: When opening, upper and lower surfaces: Close to 76B. Fully opened, upper and lower surfaces: Close to 76B to 76C.

*Sepals (present on both fertile and sterile flowers).*—Quantity per flower: About four. Length: Fertile flowers: About 1.5 mm. Sterile flowers: About 1.2 cm. Width: Fertile flowers: About 1 mm. Sterile flowers: About 1.3 mm. Shape: Fertile flowers: Linear. Sterile flowers: Ovate. Apex: Fertile flowers: Acute. Sterile flowers: Acute to obtuse. Base: Fertile flowers: Obtuse. Sterile flowers: Obtuse to attenuate. Margin, fertile and sterile flowers: Entire. Texture, fertile and sterile flowers, upper and lower surfaces: Smooth, glabrous. Color: Fertile flowers, when opening and fully opened, upper and lower surfaces: Close to 144A. Sterile flowers: When opening and fully opened, upper surface: Close to 76B. When opening and fully opened, lower surface: Close to 76B to 76C.

*Peduncles.*—Length: About 6 cm. Diameter: About 3 mm. Strength: Strong. Texture: Smooth. Color: Close to 144A.

*Pedicels.*—Length: Fertile flowers: About 5 mm. Sterile flowers: About 2.5 cm. Diameter: Fertile flowers: About 0.5 mm. Sterile flowers: About 1 mm. Strength, fertile and sterile flowers: Strong. Texture, fertile and sterile flowers: Smooth. Color: Fertile flowers: Close to 76B. Sterile flowers: Close to 76B to 76C.

*Reproductive organs (reproductive organs present only on fertile flowers; sterile flowers do not have reproductive organs).*—Stamens: Quantity per flower: About ten. Anther shape: Round. Anther length: About 0.5 mm. Anther color: Close to 201D. Pollen amount: None observed. Pistils: Pistil quantity per flower: About four. Pistil length: About 1 mm. Stigma shape: Elongate. Stigma color: Close to 76A. Style length: Less than 1 mm. Style color: Close to 76B to 76C. Ovary color: 144A. Seed/fruit: Seed and fruit development has not been observed.

Disease/pest resistance: Under commercial production conditions plants of the new *Hydrangea* have not been observed to be resistant to pathogens or pests common to *Hydrangea.*

Temperature tolerance: Plants of the new *Hydrangea* have been shown to be tolerant to temperatures ranging from −5° C. to more than 35° C.

It is claimed:

1. A new and distinct cultivar of *Hydrangea* plant named 'Summer Frost', as illustrated and described.

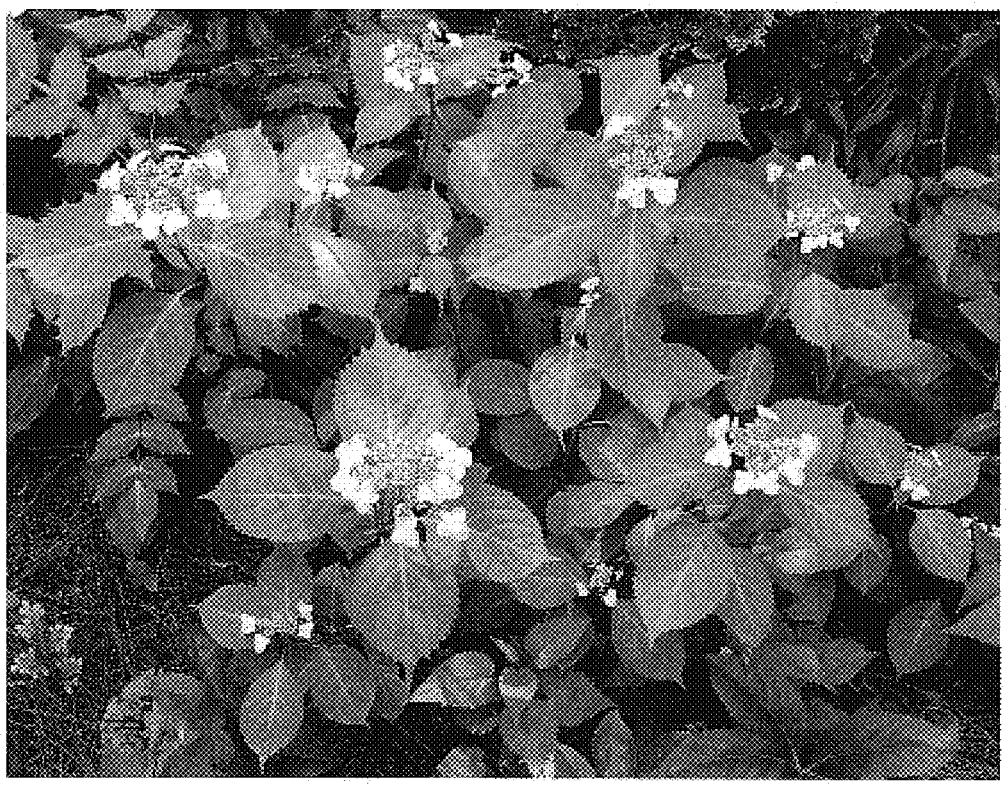

* * * * *